(12) United States Patent
Mansour et al.

(10) Patent No.: US 12,201,799 B2
(45) Date of Patent: Jan. 21, 2025

(54) NEEDLELESS CONNECTOR WITH IN-LINE FILTER

(71) Applicant: CareFusion 303, Inc., San Diego, CA (US)

(72) Inventors: George Mansour, Diamond Bar, CA (US); James Paloyan, Park Ridge, IL (US)

(73) Assignee: CareFusion 303, Inc., San Diego, CA (US)

( * ) Notice: Subject to any disclaimer, the term of this patent is extended or adjusted under 35 U.S.C. 154(b) by 1266 days.

(21) Appl. No.: 16/822,759

(22) Filed: Mar. 18, 2020

(65) Prior Publication Data
US 2020/0297987 A1 Sep. 24, 2020

Related U.S. Application Data

(60) Provisional application No. 62/820,514, filed on Mar. 19, 2019.

(51) Int. Cl.
*A61M 39/02* (2006.01)
*A61M 39/22* (2006.01)

(52) U.S. Cl.
CPC ........ *A61M 39/0208* (2013.01); *A61M 39/22* (2013.01); *A61M 2039/0241* (2013.01)

(58) Field of Classification Search
CPC .. A61M 2005/1652; A61M 2039/0241; A61M 2039/1061; A61M 2039/1072; A61M 2205/7563; A61M 39/0208; A61M 39/10; A61M 39/22
See application file for complete search history.

(56) References Cited

U.S. PATENT DOCUMENTS

| | | | |
|---|---|---|---|
| 4,127,131 A * | 11/1978 | Vaillancourt | A61M 5/165 29/451 |
| 4,259,187 A | 3/1981 | DeFrank et al. | |
| 4,935,002 A * | 6/1990 | Gordon | B01D 63/084 210/780 |

(Continued)

FOREIGN PATENT DOCUMENTS

| CA | 2218999 A1 | 10/1996 |
|---|---|---|
| CN | 1658923 A | 8/2005 |

(Continued)

OTHER PUBLICATIONS

International Search Report and Written Opinion for Application No. PCT/US2020/023306, dated Jun. 3, 2020, 13 pages.

(Continued)

*Primary Examiner* — Brandy S Lee
(74) *Attorney, Agent, or Firm* — Morgan, Lewis & Bockius LLP

(57) ABSTRACT

Needleless connectors are described herein. A needleless connector includes a housing comprising a cavity and a proximal fluid port in fluid communication with the cavity. The connector further includes a filter support disposed at least partially within the cavity. The filter support can include a distal fluid port in fluid communication with the proximal fluid port. The connector further includes a filter disposed circumferentially around the filter support and between the proximal fluid port and the distal fluid port.

18 Claims, 8 Drawing Sheets

(56) References Cited

U.S. PATENT DOCUMENTS

| | | | |
|---|---|---|---|
| 6,416,293 B1* | 7/2002 | Bouchard | F04B 43/107 |
| | | | 417/313 |
| 2006/0173490 A1 | 8/2006 | Lafontaine et al. | |
| 2006/0264897 A1* | 11/2006 | Lobl | A61P 27/16 |
| | | | 604/117 |
| 2008/0027401 A1 | 1/2008 | Ou-Yang et al. | |
| 2008/0300542 A1* | 12/2008 | Kitani | A61M 39/26 |
| | | | 604/131 |
| 2012/0192968 A1 | 8/2012 | Bonnal et al. | |
| 2016/0339226 A1 | 11/2016 | Sealfon | |

FOREIGN PATENT DOCUMENTS

| | | | | |
|---|---|---|---|---|
| CN | 107820438 A | | 3/2018 | |
| JP | S5466589 A | | 5/1979 | |
| JP | 2000084072 A | | 3/2000 | |
| JP | 2005524497 A | * | 8/2005 | ............ A61M 39/02 |
| JP | 2007195933 A | | 8/2007 | |
| JP | 2008537684 A | | 9/2008 | |
| JP | 2009273515 A | | 11/2009 | |

OTHER PUBLICATIONS

India Office Action for Application No. 202117042165, dated Apr. 25, 2023, 9 pages.

Chinese Office Action for Application No. 202080022248.1, dated Feb. 27, 2024, 22 pages including translation.

Japanese Office Action for Application No. 2021-556216, dated Jan. 19, 2024, 8 pages including translation.

Chinese Office Action for Application No. 202080022248.1, dated Jun. 28, 2024, 22 pages including translation.

European Office Action for Application No. 20719813.6, dated Nov. 21, 2024, 5 pages.

Australian Office Action for Application No. 2020241980, dated Sep. 25, 2024, 3 pages.

* cited by examiner

NEEDLELESS CONNECTOR WITH IN-LINE FILTER

CROSS-REFERENCE TO RELATED APPLICATIONS

This application claims benefit of priority under 35 U.S.C. § 119 from U.S. Patent Application 62/820,514 filed Mar. 19, 2019, which is incorporated herein by reference in its entirety.

FIELD OF THE INVENTION

The present disclosure generally relates to connectors, and, in particular, to needleless connectors.

BACKGROUND

Medical treatments often include the infusion of a medical fluid (e.g., a saline solution or a liquid medication) to patients using an intravenous (IV) catheter that is connected though an arrangement of flexible tubing and fittings, commonly referred to as an "IV set," to a source of fluid, for example, an IV bag. Certain needleless connectors may be used in an IV set and may have a self-sealing port to prevent leakage of fluid when a mating medical implement is decoupled from such a needleless connector. Additionally, a needleless connector may include a mechanical valve, for example, a collapsible valve comprising a flexible material for providing the self-sealing port and controlling the flow of fluid within the IV set.

In some applications, during the use of IV catheters, blood infections may be caused by bacteria and other microorganisms that may be introduced into the IV set.

SUMMARY

The disclosed subject matter relates to connectors having filters. In certain embodiments, a needleless connector is disclosed that comprises a housing comprising a cavity and a proximal fluid port in fluid communication with the cavity; a filter support disposed at least partially within the cavity, the filter support comprising a distal fluid port in fluid communication with the proximal fluid port; and a filter disposed circumferentially around the filter support and between the proximal fluid port and the distal fluid port.

In certain embodiments, a needleless connector is disclosed that comprises a housing comprising a cavity and a proximal fluid port in fluid communication with the cavity; a filter support disposed at least partially within the cavity, the filter support comprising a distal fluid port in fluid communication with the proximal fluid port, the housing and the filter support defining a flow path between the proximal fluid port and the distal fluid port; and a filter disposed around the filter support, wherein the filter is selectively removed from the flow path.

In certain embodiments, a method to selectively filter a fluid flow is disclosed that comprises introducing a first fluid flow from a first fluid port into a needleless connector; directing the first fluid flow through a filter disposed within the needleless connector; and directing the first fluid flow to a second fluid port out of the needleless connector.

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

Figure 1:
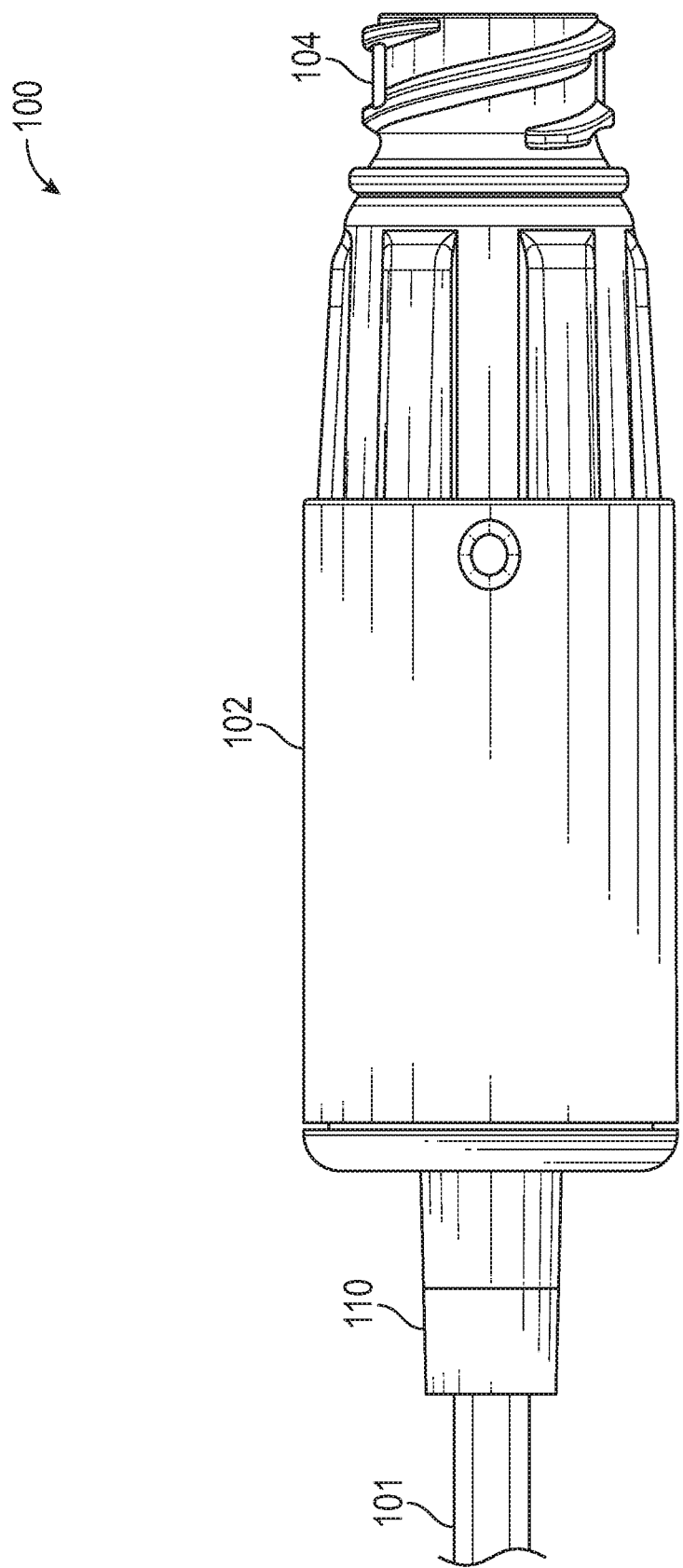
FIG. 1 is an elevation view of a needleless connector, in accordance with various aspects of the present disclosure.

The disclosed filtering, needleless connector incorporates a filter disposed within a body of the connector. An in-line filter can be disposed within the needleless connector to permit the filtration of fluids delivered via the connector. By filtering fluids and medicines delivered via the connector, the transfer of bacteria, microorganisms, and other pathogens to the patient can be reduced. Further, the in-line filter can be configured to bypassed during the draw of blood or other fluids from the patient to permit fluid flow of viscous fluids through the connector.

The detailed description set forth below is intended as a description of various configurations of the subject technology and is not intended to represent the only configurations in which the subject technology may be practiced. The detailed description includes specific details for the purpose of providing a thorough understanding of the subject technology. However, it will be apparent to those skilled in the art that the subject technology may be practiced without these specific details. In some instances, well-known structures and components are shown in block diagram form in order to avoid obscuring the concepts of the subject technology. Like components are labeled with identical element numbers for ease of understanding. Reference numbers may have letter suffixes appended to indicate separate instances of a common element while being referred to generically by the same number without a suffix letter.

While the following description is directed to the administration of medical fluid to a patient by a medical practitioner using the disclosed needleless connector, it is to be understood that this description is only an example of usage and does not limit the scope of the claims. Various aspects of the disclosed needleless connectors may be used in any application where it is desirable to prevent the transfer of bacteria, microorganisms, and other pathogens while permitting the draw of blood and other fluids from the patient.

The disclosed needleless connector overcomes several challenges discovered with respect to certain conventional connectors. One challenge with certain conventional needleless self-sealing connectors is that bacteria, microorganisms, and other pathogens may be transferred to a patient during use of an IV set. Because such a transfer of pathogens may lead to an infection, such a transfer is undesirable. Another challenge with certain needleless self-sealing connectors is that the flow of blood or other fluids from a patient to a collection or conditioning device may be restricted or not possible.

Therefore, in accordance with the present disclosure, it is advantageous to provide a needleless connector as described herein that eliminates or substantially reduces the potential transfer of pathogens to the patient while permitting blood or other fluids from the patient to be drawn. The disclosed needleless connector provides an in-line filter that prevents the transfer of pathogens to the patient and that can be bypassed to allow patient fluids to be drawn.

An example of a needleless connector that eliminates or substantially reduces the transfer of pathogens while permitting the flow of patient fluid is now described.

FIG. 1 is an elevation view of a needleless connector 100, in accordance with various aspects of the present disclosure. In the depicted example, the needleless connector 100 is a self-sealing port that provides IV access to a patient while further preventing leakage of fluid when the mating medical implement is decoupled from the needleless connector 100. As illustrated, fluid flow from an IV set can be introduced into a patient via a proximal fluid port 104, through a housing 102, through the distal fluid port 110 and to a patient via a patient tubing 101. Further, in some embodiments, blood and other fluids from the patient can be drawn from the distal fluid port 110 through the housing 102 to the proximal fluid port 104. As shown, the proximal fluid port 104 and the distal fluid port 110 can include any suitable fitting, including, but not limited to Luer fittings. In the depicted example, the proximal fluid port 104 is shown as a female Luer fitting and the distal fluid port 110 is shown as a male Luer fitting.

Further, as described herein, fluid flow through the needleless connector 100 can be filtered to prevent the transfer of bacteria, microorganisms, and other pathogens to the patient, while permitting the draw of blood and other fluids from the patient.

Figure 2:
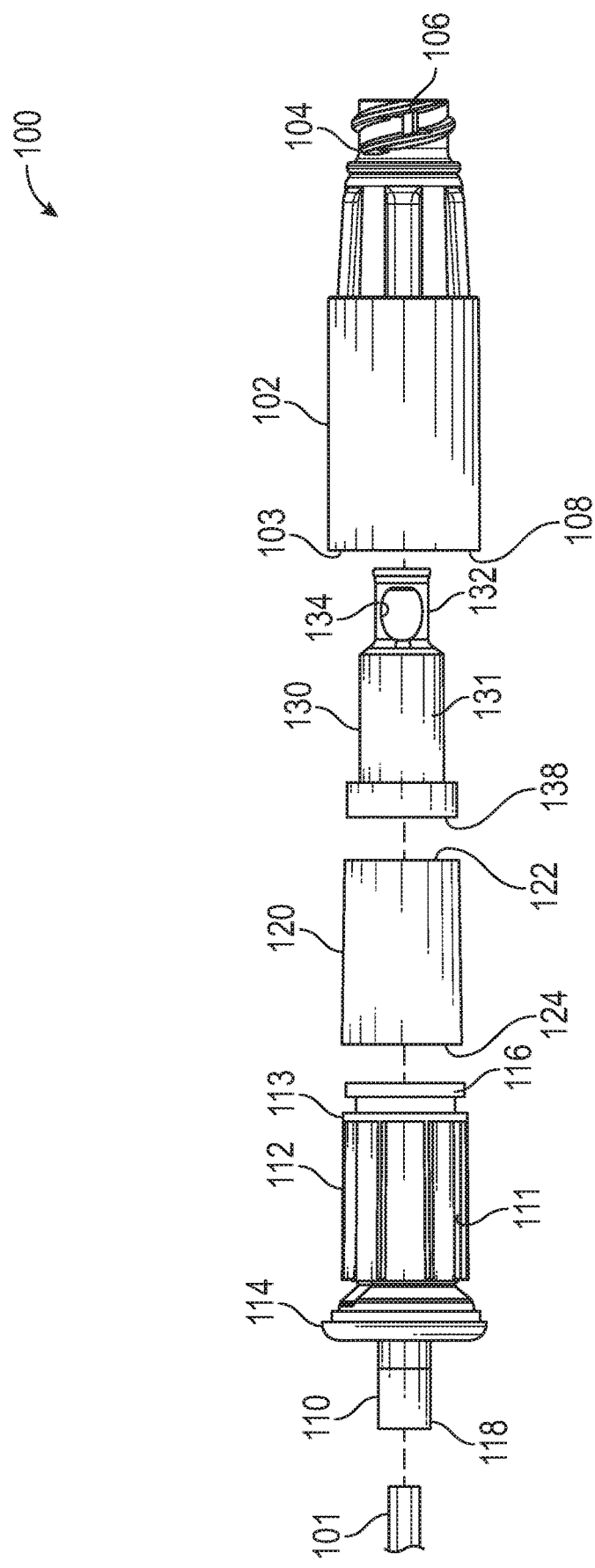
FIG. 2 is an exploded view of the needleless connector of FIG. 1, in accordance with various aspects of the present disclosure.

FIG. 2 is an exploded view of the needleless connector 100 of FIG. 1, in accordance with various aspects of the present disclosure. As illustrated, the housing 102 of the needleless connector 100 contains the flexible valve element 130, the filter 120, and the filter support 111 within the cavity 103 of the housing 102. In the depicted example, the proximal fluid port 104 is in fluid communication with the cavity 103 of the housing 102. The proximal fluid port 104 can be threaded to facilitate connections with mating medical implements.

As illustrated, the flexible valve element 130 can permit or restrict flow through the proximal fluid port 104 by selectively sealing against the inner cavity 103 of the housing 102. The flexible valve element 130 can have a body 131 with a sealing portion 132 disposed toward the proximal end 136 of the flexible valve element 130. The sealing portion 132 can further include a cut portion 134 to facilitate flow past the flexible valve element 130 by readily deforming upon insertion of a mating medical implement. The body 131 of the flexible valve element 130 can be formed from silicone or other elastomeric materials to resiliently deform and reform to allow selective sealing of the proximal fluid port 104. The flexible valve element 130 can be coupled with the filter support 111 via a distal flange 138.

When flow through the housing 102 is permitted by the flexible valve element 130, the filter 120 can selectively filter the flow through the needleless connector 100. In some embodiments, the filter 120 can comprise a filter medium configured to prevent the transfer of bacteria, microorganisms, and/or other pathogens. The filter 120 can have an average filter opening of approximately 0.2 microns. Optionally, the average filter opening of the filter 120 can range between 0.1 microns to 10 microns. The filter 120 can be formed of a resilient or expandable material.

As illustrated, the filter 120 can have a generally cylindrical or frustroconical shape. For example, the proximal end 122 of the filter 120 tapers to a generally smaller radius than the distal end 124 of the filter 120. In some embodiments, the proximal end 122 and the distal end 124 can have a same or similar radius.

As shown, the filter 120 can be supported by the filter support 111 to allow a flow path through the filter 120. In the depicted example, the filter support 111 can have a rigid construction and can include axial ribs 112 and circumferential ribs 113 to support the filter 120 while facilitating flow through the filter. Therefore, the filter 120 can be radially spaced apart from the body of the filter support 111.

Optionally, the proximal end 116 of the filter support 111 can engage the distal flange 138 of the flexible valve element 130. Accordingly, the filter 120 can be axially retained between the support flange 114 of the support frame 111 and the distal flange 138 of the flexible valve element 130.

As illustrated, the filter support 111 can further facilitate fluid flow through the distal end 118 of the filter support 111. In the depicted example, the filter support 111 includes the distal fluid port 110 disposed on the distal end 118 of the filter support 111. The distal fluid port 110 can be in fluid communication with the interior surface of the filter 120 and the cavity 103 generally. The distal fluid port 110 can be coupled to the patient tubing 101. As described herein, a flow from the proximal fluid port 104 to the distal fluid port 110 may flow through the filter 120 while a flow from the distal fluid port 110 to the proximal fluid port 104 may bypass the filter 120.

Figure 3:
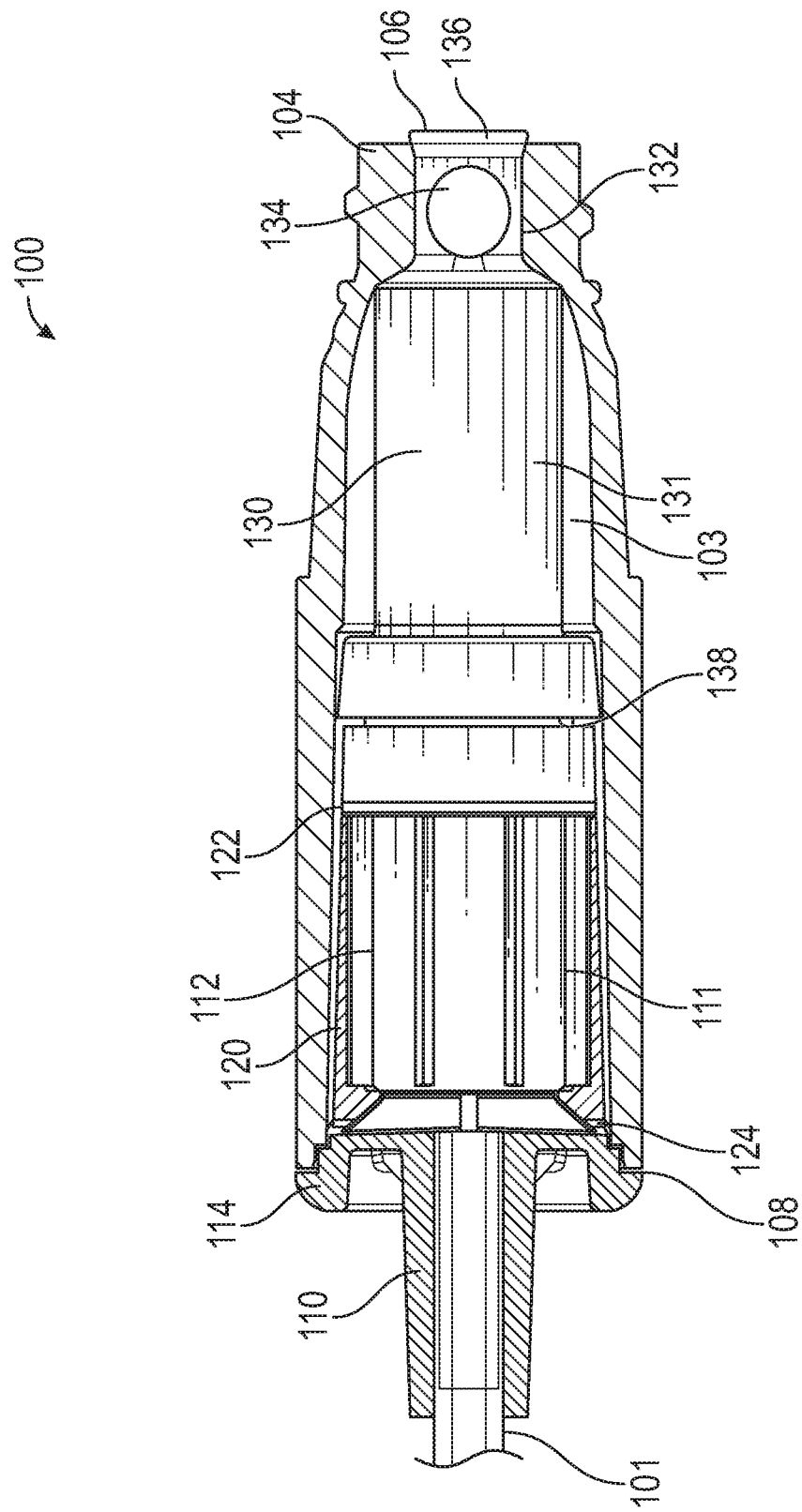
FIG. 3 is a cross-sectional view of the needleless connector of FIG. 1 in a sealing configuration, in accordance with various aspects of the present disclosure.

FIG. 3 is a cross-sectional view of the needleless connector of FIG. 1 in a sealing configuration, in accordance with various aspects of the present disclosure. In the depicted example, the flexible valve element 130 forms a seal to prohibit the flow of fluid through the proximal fluid port 104 and the needleless connector 100 generally when a mating medical implement is not connected to the proximal fluid port 104, thereby preventing leakage. Accordingly, when the needleless connector 100 is not being accessed, the sealing portion 132 and the flexible body 131 of the flexible valve element 130 generally seal against the interior cavity 103 to prevent fluid flow therethrough.

Figure 4:
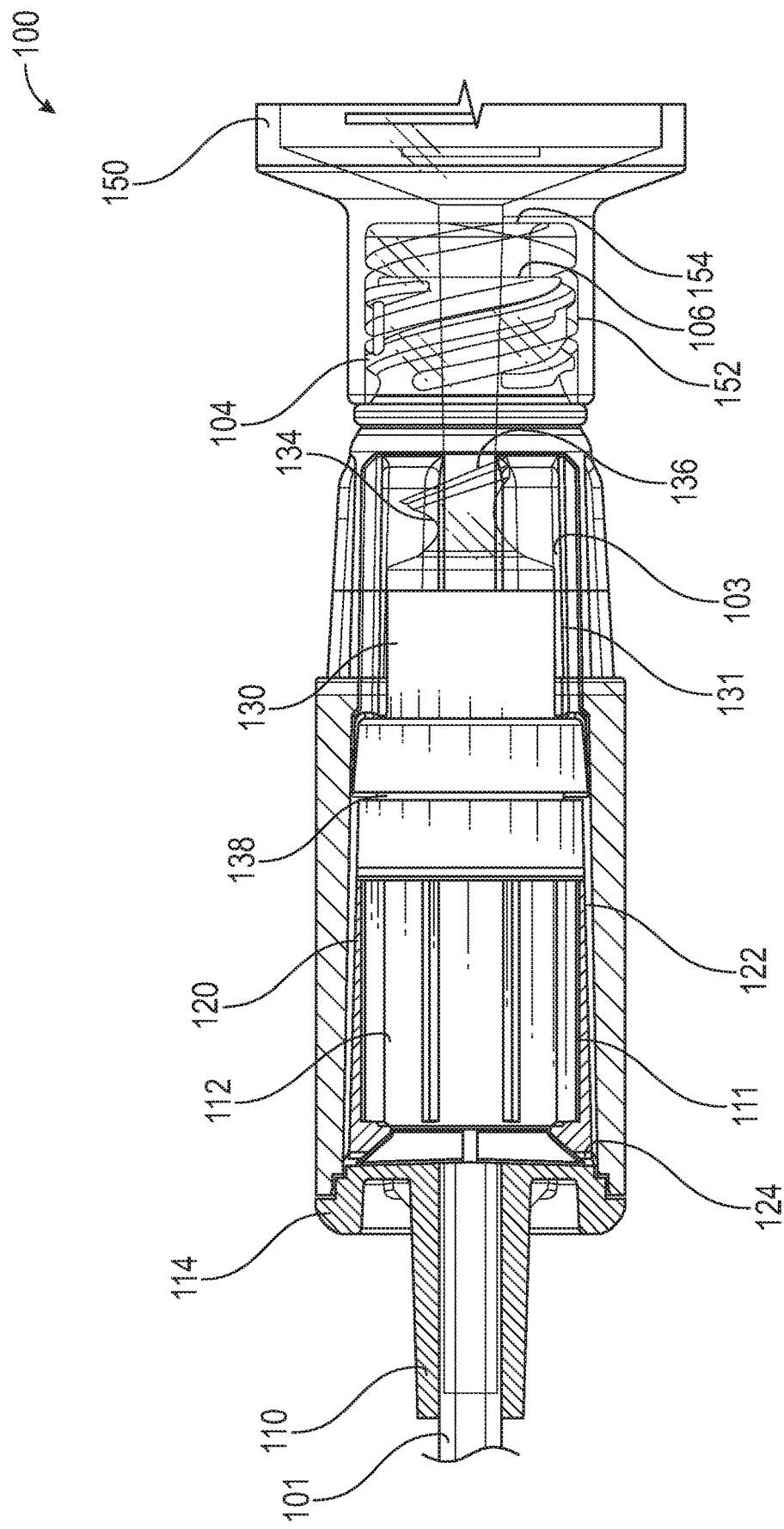
FIG. 4 is a cross-sectional view of the needleless connector of FIG. 1 in a flowing configuration, in accordance with various aspects of the present disclosure.

FIG. 4 is a cross-sectional view of the needleless connector of FIG. 1 in a flowing configuration, in accordance with various aspects of the present disclosure. As illustrated, a mating medical implement 150 can be attached to the needleless connector 100. The medical implement 150 can be used to introduce a fluid or medicine to the patient or to draw blood or other fluids from the patient via the needleless connector 100. The medical implement 150 can be connected to the proximal flow port 104 via a threaded connection 152.

During operation, the male fitting 154 of the medical implement 150 can be introduced into the cavity 103 of the housing 102. Upon introduction of the male fitting 154 into the cavity 103, the flexible valve element 130 can be sufficiently elastic to deform or bend out of sealing engagement with the cavity 103 to permit fluid flow between the needleless connector 100 and the medical implement 150. The flexible valve element 130 can return to its original shape upon disconnection of the male fitting 154. The flexible valve element 130 is shown in a collapsed position, allowing fluid flow between the distal fluid port 110 and the proximal flow port 104.

In the depicted example, the needleless connector 100 can be a positive displacement device. For example, when a new connection is made at the proximal fluid port 104, the volume of the internal cavity 103 is reduced, and the needleless connector 100 draws fluid in from the proximal fluid port 104 or the distal fluid port 110. Accordingly, when disconnection is made at the proximal fluid port 104, the needleless connector 100 expels fluid from the cavity 103, effectively flushing the needleless connector 100. Advantageously, the filter 120 can dampen or otherwise control the expulsion of fluid from the cavity 103.

Figure 5:
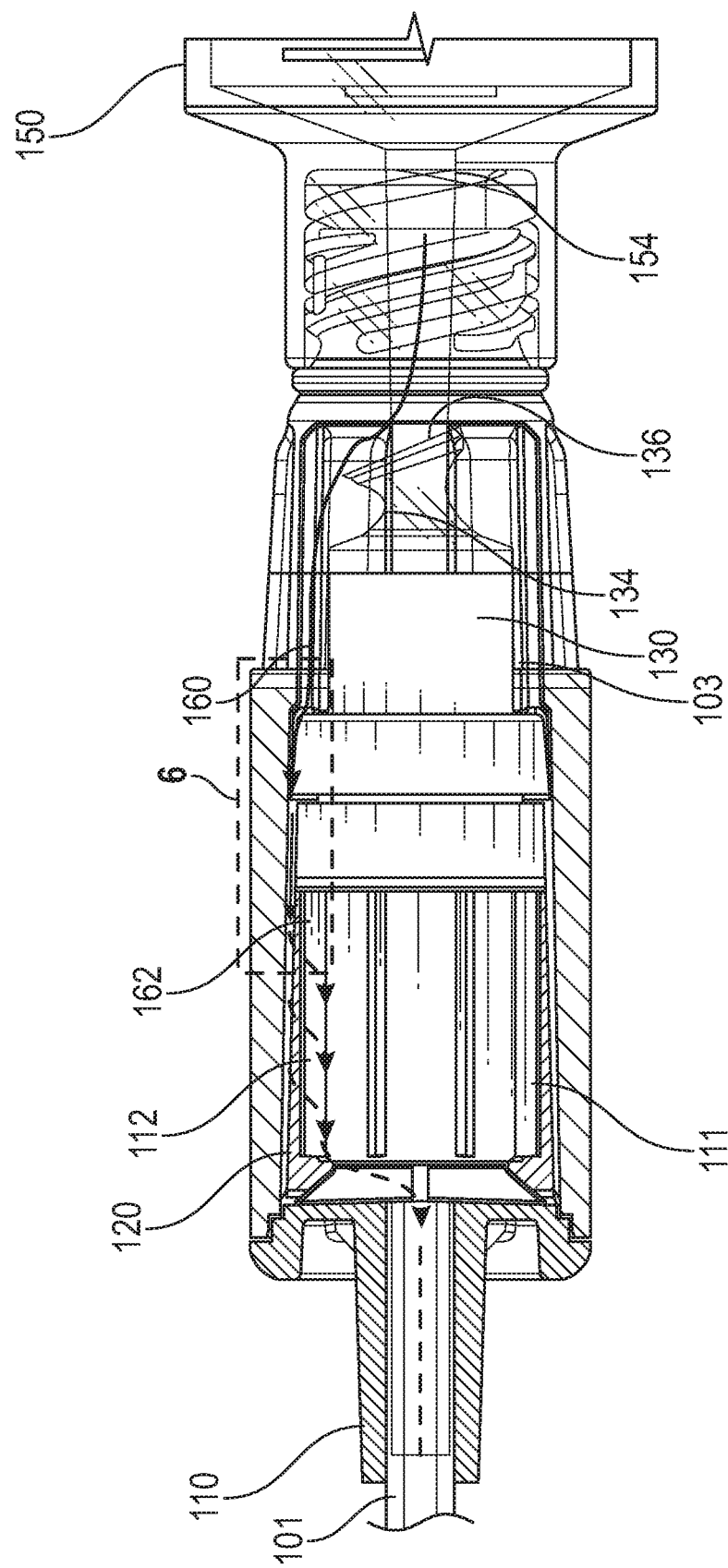
FIG. 5 is a cross-sectional view of the needleless connector of FIG. 4 with flow directed from a generally proximal to distal direction, in accordance with various aspects of the present disclosure.

FIG. 5 is a cross-sectional view of the needleless connector of FIG. 4 with flow 160 directed from a generally proximal to distal direction, in accordance with various aspects of the present disclosure. As illustrated, when fluid is introduced from the medical implement 150 into the patient such as when introducing saline or medicine into a patient, the flow 160 illustrates the path of the fluid from the proximal fluid port 104 to the distal fluid port 110 and into the patient tubing 101. In the depicted example, the flow 160 is directed from the medical implement 150 towards the cavity 103. The bent or deformed flexible valve element 130 allows for the flow to pass beyond the proximal fluid port 104 and continue towards the filter 120.

Figure 6:
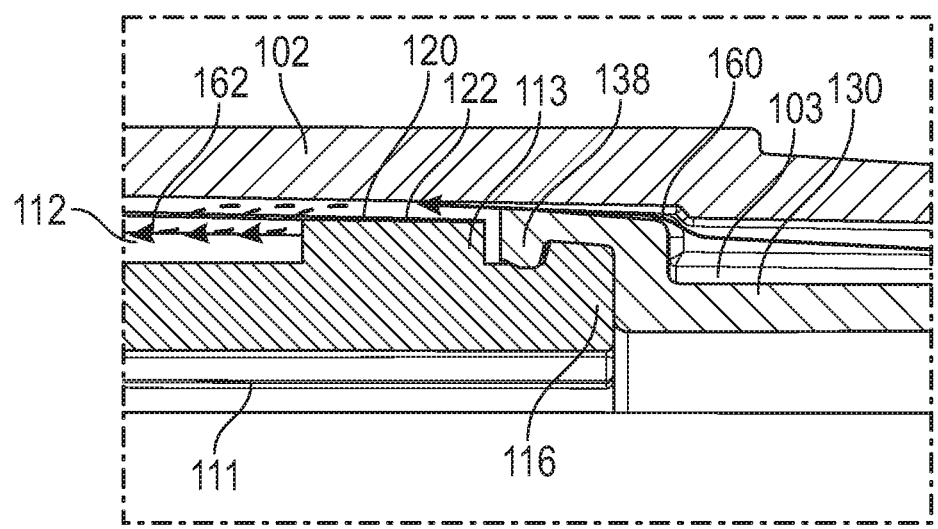
FIG. 6 is a detail view of the proximal end of the filter of FIG. 5, in accordance with various aspects of the present disclosure.

FIG. 6 is a detail view of the proximal end 122 of the filter 120 of FIG. 5, in accordance with various aspects of the present disclosure. As shown in FIG. 6, the fluid flow 160 passes through the filter 120. The resulting filtered flow 162 continues through the filter support 111, through the distal flow port 110 to the patient tubing 101.

In the depicted example, as the fluid flow 160 flows in a general proximal to distal direction, the force imparted against the outer surface of the filter 120 by the fluid flow 160 urges the filter 120 against the axial ribs 112 and the circumferential ribs 113 of the filter support 111. Advantageously, this ensures that the fluid of the flow path 160 is filtered via the filter 120, permitting introduced fluids such as saline and/or medications to be filtered to prevent the transfer of bacteria to a patient.

Figure 7:
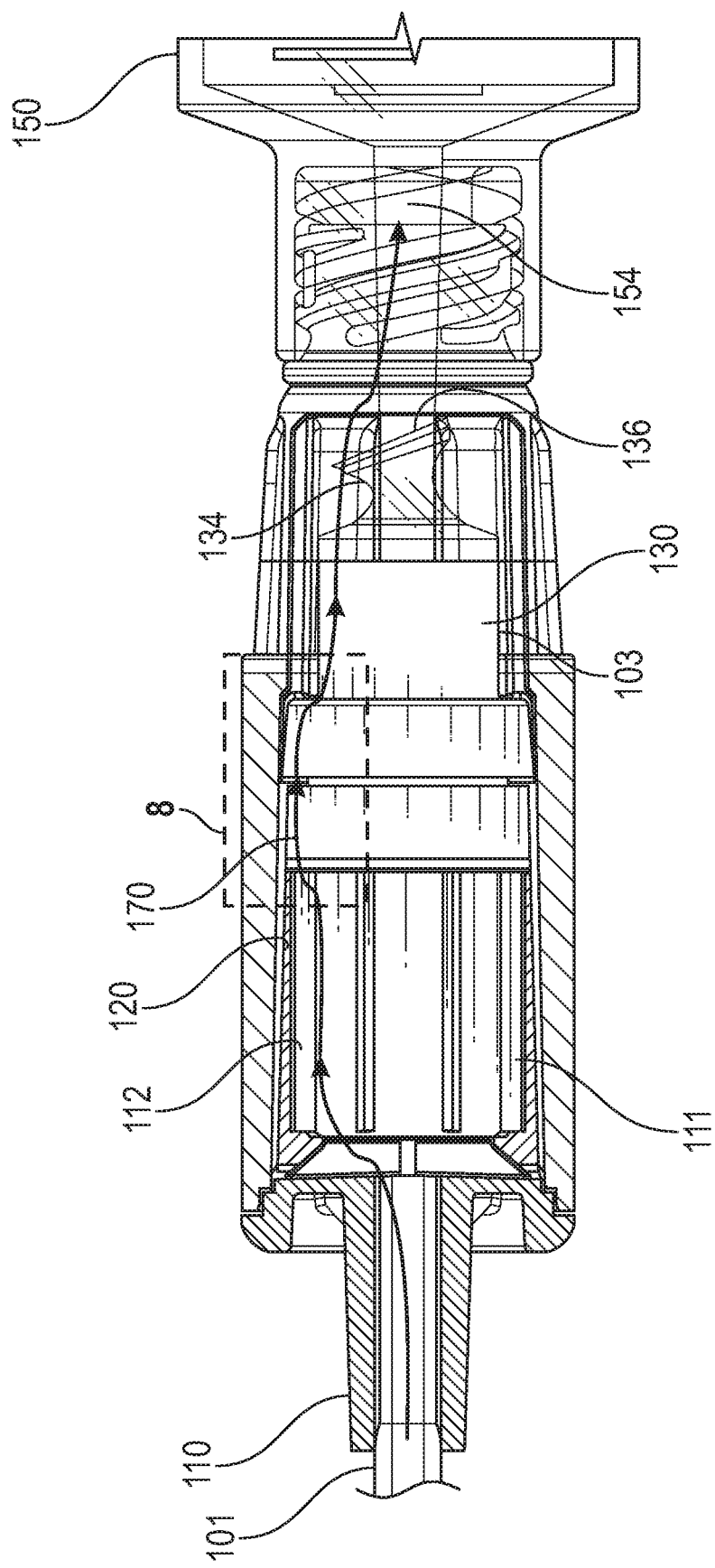
FIG. 7 is a cross-sectional view of the needleless connector of FIG. 4 with flow directed from a generally distal to proximal direction, in accordance with various aspects of the present disclosure.

FIG. 7 is a cross-sectional view of the needleless connector 100 of FIG. 4 with flow 170 directed from a generally distal to proximal direction, in accordance with various aspects of the present disclosure. As illustrated, when fluid is drawn from the patient, such as when blood is drawn, the flow 170 illustrates the path of the fluid from the distal fluid port 110 to the proximal fluid port 104 and further to the medical implement 150. In the depicted example, drawn fluid from the patient is directed from the distal fluid port 110 toward the filter 120. The drawn fluid may bypass the filter 120 and continue past the bent or deformed flexible valve element 130 to allow the flow to continue to the proximal fluid port 104.

Figure 8:
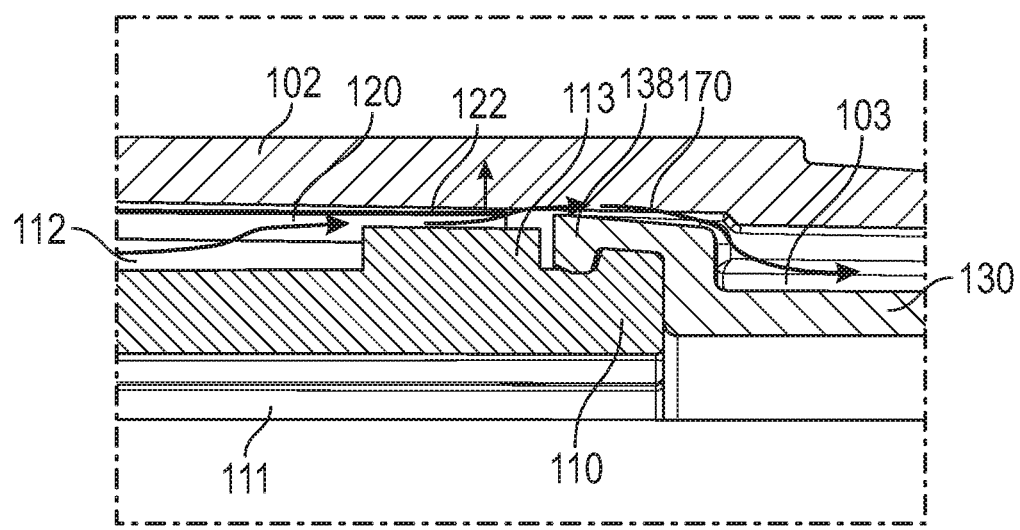
FIG. 8 is a detail view of the proximal end of the filter of FIG. 7, in accordance with various aspects of the present disclosure.

FIG. 8 is a detail view of the proximal end 122 of the filter 120 of FIG. 7, in accordance with various aspects of the present disclosure. In the depicted example, the fluid flow 170 bypasses the filter 120. In some embodiments, the filter 120 may be bypassed in response to the direction of flow 170 through the needleless connector 100. For example, the filter 120 may be bypassed when blood or other patient fluids flow from the distal fluid port 110 to the proximal fluid port 104, as shown in fluid flow 170. Optionally, other characteristics of the fluid flow 170, such as fluid viscosity can be utilized to bypass the filter 120.

Advantageously, the filter 120 can be bypassed by radially expanding the filter 120, creating an alternative flow path toward the proximal flow port 104 without filtration. For example, the force imparted against the inner surface of the filter 120 by the fluid flow 170 may urge the filter 120 to radially expand away from the filter support 111. In particular, the filter 120 may be urged, expanded, or stretched radially away from the axial ribs 112 and/or the circumferential ribs 113, creating an alternative flow path toward the proximal flow port 104. In some embodiments, the proximal end 122 of the filter 120 can radially expand to permit bypass flow. Optionally, fluid flows 170 with increased viscosity may further expand the filter 120.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

In one aspect, the term "coupled" or the like may refer to being directly coupled. In another aspect, the term "coupled" or the like may refer to being indirectly coupled.

Terms such as "top," "bottom," "front," "rear" and the like if used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Various items may be arranged differently (e.g., arranged in a different order, or partitioned in a different way) all without departing from the scope of the subject technology. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but is to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A needleless connector, comprising:
   a housing comprising a cavity and a proximal fluid port in fluid communication with the cavity;
   a filter support disposed at least partially within the cavity, the filter support comprising a distal fluid port in fluid communication with the proximal fluid port; and
   a filter disposed circumferentially around the filter support and between the proximal fluid port and the distal fluid port, wherein a proximal end of the filter radially expands away from the filter support to prevent fluid flow through a filter medium to the proximal fluid port.

2. The needleless connector of claim 1, wherein the filter comprises a conical shape.

3. The needleless connector of claim 2, wherein a distal end of the filter comprises a first radius and the proximal end of the filter comprises a second radius, and the first radius is greater than the second radius.

4. The needleless connector of claim 1, wherein the filter comprises an average filter opening of 0.2 microns.

5. The needleless connector of claim 1, wherein the proximal end of the filter is in contact with a circumferential rib of the filter support.

6. The needleless connector of claim 1, wherein the filter support comprises a rigid material.

7. The needleless connector of claim 1, wherein the filter support comprises a plurality of axial ribs to support the filter.

8. The needleless connector of claim 1, further comprising a flexible valve element disposed within the cavity to selectively permit flow between the proximal fluid port and the distal fluid port.

9. The needleless connector of claim 1, wherein the proximal end of the filter comprises an expandable radius to prevent fluid flow through the filter medium to the proximal fluid port.

10. A needleless connector, comprising:
    a housing comprising a cavity and a proximal fluid port in fluid communication with the cavity;
    a filter support disposed at least partially within the cavity, the filter support comprising a distal fluid port in fluid communication with the proximal fluid port, the housing and the filter support defining a flow path between the proximal fluid port and the distal fluid port; and
    a filter disposed around the filter support, wherein the filter is expandable to be removed from the flow path.

11. The needleless connector of claim 10, wherein a distal end of the filter comprises a first radius and a proximal end of the filter comprises a second radius, and the first radius is greater than the second radius.

12. The needleless connector of claim 10, wherein the filter comprises a conical shape.

13. The needleless connector of claim 10, wherein a proximal end of the filter comprises an expandable radius to remove the filter from the flow path.

14. The needleless connector of claim 13, wherein the proximal end of the filter radially expands away from the filter support.

15. A method to selectively filter a fluid flow, the method comprising:
    introducing a first fluid flow from a first fluid port into a needleless connector;
    directing the first fluid flow through a filter disposed within the needleless connector;

directing the first fluid flow to a second fluid port out of the needleless connector;

imparting a force against an inner surface of the filter via a second fluid flow to radially expand the filter; and expanding the filter to prevent fluid flow through a filter medium to the second fluid port.

16. The method of claim 15, further comprising:

introducing the second fluid flow from the second fluid port into the needleless connector;

bypassing the filter disposed within the needleless connector; and directing the second fluid flow to the first fluid port out of the needleless connector.

17. The method of claim 15, further comprising:

expanding a radius of the proximal end of the filter to prevent fluid flow through the filter medium to the second fluid port.

18. A method to selectively filter a fluid flow, the method comprising:

introducing a first fluid flow from a first fluid port into a needleless connector;

directing the first fluid flow through a filter disposed within the needleless connector;

selectively permitting the first fluid flow through a filter medium of the filter;

directing the first fluid flow to a second fluid port out of the needleless connector;

imparting a force against an inner surface of the filter via a second fluid flow to radially expand the filter;

introducing the second fluid flow from the second fluid port into the needleless connector;

bypassing the filter disposed within the needleless connector; and directing the second fluid flow to the first fluid port out of the needleless connector.

\* \* \* \* \*